US009365891B2

(12) United States Patent
Hamasaki et al.

(10) Patent No.: US 9,365,891 B2
(45) Date of Patent: Jun. 14, 2016

(54) NUCLEIC ACID ANALYSIS DEVICE, METHOD FOR PRODUCING SAME, AND NUCLEIC ACID ANALYZER

(71) Applicant: HITACHI HIGH-TECHNOLOGIES CORPORATION, Tokyo (JP)

(72) Inventors: Koshin Hamasaki, Hitachinaka (JP); Toshiro Saito, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/642,461

(22) Filed: Mar. 9, 2015

(65) Prior Publication Data
US 2015/0184227 A1    Jul. 2, 2015

Related U.S. Application Data

(62) Division of application No. 13/697,019, filed as application No. PCT/JP2011/060637 on May 9, 2011, now abandoned.

(30) Foreign Application Priority Data

May 10, 2010 (JP) .................................. 2010-108003

(51) Int. Cl.
| C12Q 1/68 | (2006.01) |
| G01N 21/64 | (2006.01) |
| G01N 33/543 | (2006.01) |
| G01N 21/552 | (2014.01) |
| G01N 21/05 | (2006.01) |

(52) U.S. Cl.
CPC ............ *C12Q 1/6806* (2013.01); *C12Q 1/6834* (2013.01); *G01N 21/554* (2013.01); *G01N 21/648* (2013.01); *G01N 33/54346* (2013.01); *G01N 21/05* (2013.01)

(58) Field of Classification Search
CPC ...................... G01N 33/54346; G01N 21/554
USPC ............................................. 506/30
See application file for complete search history.

(56) References Cited

U.S. PATENT DOCUMENTS 5,900,481 A * 5/1999 Lough ................... C07F 9/2408
502/233
6,024,925 A   2/2000 Little et al.
(Continued)

FOREIGN PATENT DOCUMENTS

AU    2002300406 B9 * 11/2005

OTHER PUBLICATIONS

Ahn et al. (ACSNANO, 2010, vol. 4, No. 7, pp. 4181-4189).*
(Continued)

*Primary Examiner* — Larry Riggs
*Assistant Examiner* — Karla Dines
(74) *Attorney, Agent, or Firm* — Baker Botts L.L.P.

(57) ABSTRACT

Disclosed is a technique for binding microparticles to patterned bonding pads of a metal (e.g., gold) formed on a support. The microparticles each carry a nucleic acid synthetase or DNA probe immobilized thereon for capturing a nucleic acid sample fragment. The technique involves forming, on a support surface, a film having a thickness equivalent to that of the bonding pads; controlling the size of microparticles with respect to the size of bonding pads; and thereby immobilizing microparticles each bearing a single nucleic acid sample fragment to the bonding pads in a one-to-one manner in a grid form. This allows high-density regular alignment and immobilization of many types of nucleic acid fragment samples on a support and enables high-throughput analysis of nucleic acid samples. Typically, immobilization of microparticles at 1-micrometer intervals easily provides a high density of $10^6$ nucleic acid fragments per square millimeter.

8 Claims, 7 Drawing Sheets

(56) References Cited

U.S. PATENT DOCUMENTS

| | | | |
|---|---|---|---|
| 6,133,436 | A | 10/2000 | Koster et al. |
| 7,285,422 | B1 | 10/2007 | Little et al. |
| 8,043,846 | B2 * | 10/2011 | Irimia ................ B01F 13/0066 366/DIG. 2 |
| 2002/0123134 | A1 | 9/2002 | Huang et al. |
| 2002/0182483 | A1 * | 12/2002 | Miyahisa ................ H01M 4/04 429/94 |
| 2005/0079592 | A1 | 4/2005 | Takagi |
| 2007/0166741 | A1 * | 7/2007 | Heil ..................... C12Q 1/6832 435/6.15 |
| 2009/0079988 | A1 | 3/2009 | Narahara et al. |
| 2010/0304982 | A1 | 12/2010 | Hinz et al. |

OTHER PUBLICATIONS

Jans et al., 2009, Business Media, Springer Science, pp. 277-294.*
Jans et al., Sensors for Environment, Health and Security, 2009, Springer Science and Business Media, pp. 277-294.
Anderson et al., Langmuir, 2008, 24, pp. 2240-2247.
Translation of Japanese Office Action issued on Feb. 25, 2014 in connection with Japanese Patent Application No. 2012-51473.
John EID, Real-Time DNA Sequencing from Single Polymerase Molecules, Science, Jan. 2, 2009, pp. 133-138, vol. 323.
Anton Valouev, A high-resolution, nucleosome position map of *C. elegans* reveals a lack of universal sequence-dictated positioning, Genome Research, 2008, pp. 1051-1063, vol. 18.
Ahn et al., ACS Nano, 2010, 4(7), pp. 4181-4189.
Suh et al., Biomaterials, 2004, 25, pp. 557-563.
Hutter et al., Journal of Physical Chemistry, vol. 107, No. 7, Jul. 10, 2003, pp. 6497-6499.
Marcel Margulies et al., Genome sequencing in microfabricated high-density picolitre reactors, Nature, Sep. 15, 2005, pp. 376-380, vol. 437.
Palash Bharadwaj et al., Nanoplasmonic enhancement of single-molecule fluorescence, 2007, pp. 1-5, vol. 18.
Jingyue Ju et al., Four-color DNA sequencing by synthesis using cleavable fluorescent nucleotide reversible terminators, PNAS, Dec. 26, 2006, pp. 19635-19640, vol. 103, No. 52.

* cited by examiner

NUCLEIC ACID ANALYSIS DEVICE, METHOD FOR PRODUCING SAME, AND NUCLEIC ACID ANALYZER

CROSS REFERENCE TO RELATED APPLICATIONS

This application is a divisional of U.S. patent application Ser. No. 13/697,019, filed on Nov. 9, 2012, which is a National Stage Entry of International Application No. PCT/JP2011/060637, filed on May 9, 2011, the contents of each of which are hereby incorporated by reference in their entireties.

TECHNICAL FIELD

The present invention relates to a nucleic acid analysis device, a production method thereof, and a nucleic acid analyzer using the same.

BACKGROUND ART

New techniques have been developed as nucleic acid analysis devices for determining base sequences of DNA (deoxyribonucleic acid) or RNA (ribonucleic acid). A method utilizing electrophoresis, which is now in general use, involves preparing beforehand a cDNA (complementary DNA) fragment sample synthesized through a reverse transcription reaction of a DNA fragment or an RNA sample for sequence determination; performing a dideoxy chain termination reaction by well-known Sanger's sequencing method; thereafter performing electrophoresis for the sample; and measuring a pattern of separation and development of molecular weight to analyze the pattern.

Independently, there has been recently developed a technique of immobilizing many DNA sample fragments as samples on a support so as to determine information on sequences of the many fragments in parallel. A DNA sequencer using this technique is referred to as a massively parallel sequencer. The massively parallel sequencer performs DNA elongations on fluorescence-labeled bases as a substrate in parallel at hundreds of thousands to millions of points and detects fluorescence of reacted bases to determine a DNA nucleotide sequence. Such massively parallel sequencers are categorized as those according to a cluster-basis process and those according to a single-molecule-basis process. The respective processes will be described below.

Initially, the cluster-basis process will be described. The cluster-basis process involves analysis of clusters each of which is an amplified DNA and is in the form of a bundle of DNAs. Typically, Non-Patent Literature (NPL) 1 describes a technique including: preparing microparticles bearing DNA fragments, performing polymerase chain reactions (PCRs) on the microparticles to amplify DNA fragments into many copies, and placing the microparticles bearing PCR-amplified DNA fragments in a plate having many wells, followed by pyrosequencing-based reading. The wells each have an opening with a size equal to the size of each of the microparticles.

NPL 2 describes a technique including: preparing microparticles bearing DNA fragments, performing polymerase chain reactions on the microparticles, scattering the microparticles onto a glass support, immobilizing the microparticles thereto, performing enzymatic reactions (ligation reactions) on the glass support to allow the DNA fragments to incorporate a substrate having a fluorescent dye thereinto, detecting fluorescence emitted from the fluorescent dye, and thereby obtaining information on nucleotide sequence of each of the fragments.

Next, the single-molecule-basis process will be described. The single-molecule-basis process includes: hybridizing a labeled nucleic acid with a probe without amplification, and identifying a nucleotide sequence while elongating the nucleic acid one base by one base with nucleotides each having a fluorescent dye. This technique is reported in NPL 3. Typically, the technique described in NPL 3 is a technique of preparing a plate having many wells and arranging a nucleic acid synthetase on the plate. In this technique, fluorescence is detected while allowing nucleotides having a fluorescent dye to be incorporated into a nucleic acid to thereby elongate the nucleic acid, and thus information on nucleotide sequence of each fragment is obtained.

CITATION LIST

Non-Patent Literature

NPL 1: Nature 2005, Vol. 437, pp. 376-380
NPL 2: Genome Research 200, Vol. 18, pp. 1051-1063
NPL 3: Science 2009, Vol. 323, pp. 133-138
NPL 4: Nanotechnology, 2007, Vol. 18, pp. 044017-044021.
NPL 5: P.N.A.S. 2006, Vol. 103, pp. 19635-19640

SUMMARY OF THE INVENTION

Technical Problems to be Solved by the Invention

Of massively parallel sequencers, those according to the cluster-basis process analyze DNA clusters as bundles of amplified DNAs, whereas those according to the single-molecule-basis process directly analyze DNAs without amplification. The single-molecule-basis process does not require an amplification process and can save process and running cost. The cluster-basis process is limited in base length to be read due to a dephasing phenomenon, in which sequencing reactions among plural amplified DNAs occur at different times. By contrast, the single-molecule-basis process does not theoretically undergo dephasing and indicates the possibility that bases in a significantly longer length can be read. This requires, however, a technique of immobilizing hundreds of thousands of nucleic acid sample fragments to a support on a single molecule basis or on a group of molecules basis. In this technique, maximally regular immobilization of nucleic acid samples to a flat, smooth support is desired. This is because random immobilization of microparticles bearing nucleic acid samples and being scattered on a flat, smooth support can be easily performed, but, upon reading of sequences by fluorometry, it takes an extremely long time to process numerical data, which data have been obtained from images of the microparticles being present at random, where the images are detected with a charge coupled device (CCD) camera.

Accordingly, an object of the present invention is to solve the aforementioned problems.

Solution to Problems

The present invention provides, in an aspect, a nucleic acid analysis device which comprises:
a support; a plurality of bonding pads arranged on a surface of the support;
a thin-film layer covering the surface of the support in a region other than the bonding pads;
microparticles, each of the microparticles is bound to each of the bonding pads; and a probe molecule or molecules of a single type immobilized on each of the microparticles, in which the microparticles are bound to the bonding pads through chemical bonds, and the thin-film layer is capable of suppressing non-specific adsorption of the microparticles on the surface of the support.

The present invention provides, in another aspect, a method for producing a nucleic acid analysis device which comprises the steps of:

forming a thin metal film on a surface of a support;

selectively etching the thin metal film to form a plurality of bonding pads;

introducing a linear molecule film into each of the bonding pads, the linear molecule film capable of being adsorbed on the bonding pads;

introducing microparticles onto the linear molecule film and binding the microparticles to each of the bonding pads through a chemical bond; and immobilizing a probe molecule or molecules to each of the microparticles through a chemical bond.

The present invention provides, in yet another aspect, a method for producing a nucleic acid analysis device which comprises the steps of:

forming a thin metal film on a surface of a support;

introducing a linear molecule film onto the thin metal film, the linear molecule film capable of being adsorbed on the thin metal film;

selectively etching the thin metal film and the linear molecule film and forming a plurality dummy bonding pads;

removing the dummy bonding pads to expose the linear molecule film to form a plurality each of the bonding pads having the thin metal film and the linear molecule film;

binding microparticles to each of the exposed linear molecule films through a chemical bond; and immobilizing a probe molecule or molecules to each of the microparticles through a chemical bond. As used herein the term "dummy bonding pad" corresponds to an etching mask which has a shape equivalent to that of an actual bonding pad and is formed upon patterning of a thin metal film on a linear molecule film that binds the microparticles to the thin metal films. A thin film for the suppression of non-specific adsorption of the microparticles is formed on the etching mask (dummy bonding pad), but the thin film on the etching mask will be removed together with the etching mask upon binding of the microparticles to the bonding pads.

The present invention provides, in still another aspect, a nucleic acid analyzer, which comprises:

a nucleic acid analysis device including a support and microparticles regularly immobilized on the support, the microparticles each of which has the probe molecule or molecules capable of capturing a nucleic acid to be analyzed;

a supplier for supplying a nucleic acid sample and a nucleotide having a fluorescent dye to the nucleic acid analysis device;

an irradiator for irradiating the nucleic acid analysis device with light; and an emission detector for detecting fluorescence emitted from the fluorescent dye incorporated into a nucleic acid chain through nucleic acid elongation induced by the coexistence of a nucleotide, a nucleic acid synthetase, and a nucleic acid sample. The nucleic acid analysis device, which comprises:

a plurality of bonding pads arranged on the surface of the support at positions where the microparticles are immobilized;

a thin film layer covering the surface of the support in a region other than the bonding pads;

microparticles, where a single microparticle is bound to each of the bonding pad; and a probe molecule or molecules of a single type immobilized on each of the microparticles, in which the microparticles are bound to the bonding pads through chemical bonds, and the thin film layer is capable of suppressing non-specific adsorption of the microparticles on the surface of the support.

Advantageous Effects of Invention

The present invention allows microparticles to be reliably arranged in a desired alignment and immobilized on many bonding pads in a nucleic acid analysis device and thereby enables high-precision analysis of nucleic acids with less noise.

DESCRIPTION OF EMBODIMENTS

Figure 1:
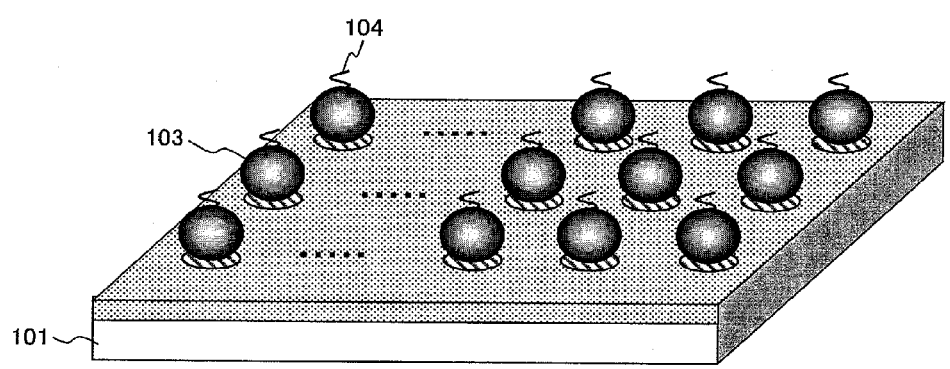
FIG. 1 is a perspective view illustrating an exemplary configuration of a nucleic acid analysis device according to an embodiment of the present invention.

The present inventors made intensive investigations on techniques for densely and regularly aligning and immobilizing nucleic acid sample fragments one by one to a support. As a result, they have found a technique for immobilizing nucleic acid sample fragments to a support one by one. This technique includes allowing microparticles to specifically react with a plurality of (preferably a multiplicity of) patterned bonding pads of a metal (such as gold) on a one-to-one basis, in which each of the microparticles have a nucleic acid synthetase or DNA probe immobilized thereto and capable of capturing a nucleic acid sample fragment. As used herein the term "one-to-one basis" refers to that a probe molecule or molecules of a single type are allowed to specifically react with one microparticle; and the number of probe molecule or molecules is not limited, as long as they are of a single type.

The present invention provides, in an embodiment, a nucleic acid analysis device which includes a support and microparticles regularly immobilized on the support, in which each of the microparticles have a probe molecule capable of capturing a nucleic acid to be analyzed, in which the nucleic acid analysis device further includes bonding pads on the support at positions where the microparticles are immobilized; the microparticles are bound to the bonding pads through chemical bonds; the nucleic acid analysis device further includes a thin-film layer on the surface of the support, and the thin-film layer is capable of suppressing or inhibiting non-specific adsorption of the microparticles; a part of each of the bonding pad is exposed from the thin-film layer; and each of the bonding pad, except for the part, is covered with the thin-film layer. The bonding pads are preferably regularly arranged on the support. Two or more probe molecules may be immobilized on a single microparticle.

More specifically, each of the microparticles bearing a substance immobilized thereto are prepared, which substance is capable of capturing a nucleic acid sample fragment and is typified by nucleic acid synthetases and DNA probes, and the microparticles are bound to bonding pads on a support, in which bonding pads include a metal such as gold and are formed in a pattern. In this process, a thin film is formed on the support, which thin film includes, for example, an organic polymer and advantageously prevents non-specific adsorption of the microparticles; the thin film of the organic polymer is designed to have a thickness equivalent to that of the bonding pads; and the sizes of the bonding pads is controlled with respect to the sizes of the microparticles. These can remarkably increase the percentage of microparticles immobilized on bonding pads in a one-to-one manner, thereby the microparticles capture and bear a single molecule of nucleic acid sample fragment.

The present invention further provides, in another embodiment, a nucleic acid analysis device which includes a support and microparticles regularly immobilized on the support, in which each of the microparticles have a probe molecule capable of capturing a nucleic acid to be analyzed; the nucleic acid analysis device further includes bonding pads on the support at positions where the microparticles are immobilized; the microparticles are bound to the bonding pads through chemical bonds; the nucleic acid analysis device further includes a thin-film layer on the support; the thin-film layer is capable of preventing non-specific adsorption of the microparticles; a part of each bonding pads is exposed from the thin-film layer; and each of the bonding pads, except for the part, is covered with or embedded in the thin-film layer.

A single molecule or two or more molecules for the probe molecule may be immobilized on a single microparticle in the nucleic acid analysis device. Two or more probe molecules, when immobilized on the single microparticle, are identical (of a single type).

The probe molecule in the nucleic acid analysis device may be a nucleic acid or a nucleic acid synthetase. The microparticles in the nucleic acid analysis device may include a material selected from the group consisting of semiconductors, metals, inorganic polymers, and organic polymers. The bonding pads preferably include a material selected from the group consisting of gold, titanium, nickel, and aluminum. The each of the bonding pads preferably have an apparent diameter of one time or less that of the microparticles.

A multiplicity (thousands to hundreds of thousands) of the bonding pads are preferably regularly arranged on the support. In an embodiment, two or more probe molecules may be immobilized on a single microparticle. This embodiment enables more simple control of the number of probes and easier production of a nucleic acid analysis device than an embodiment in which a single probe molecule is immobilized on a single microparticle. The each of the bonding pads preferably have an apparent diameter one time or less that of the microparticles.

The present invention will be illustrated with reference to several specific embodiments below. Specifically, in an embodiment, disclosed is a nucleic acid analysis device which includes a support and microparticles regularly immobilized on the support, in which each of the microparticles have a probe molecule capable of capturing a nucleic acid to be analyzed, the nucleic acid analysis device further includes bonding pads on the support at positions where the microparticles are immobilized, and the microparticles are bound to the detection pads (bonding pads) through chemical bonds.

In another embodiment, disclosed is a nucleic acid analyzer which includes a device for selectively obtaining only each of the microparticles having a single probe molecule; a nucleic acid analysis device including a support and the microparticles regularly immobilized on the support; a supplier for supplying a nucleic acid sample and a nucleotide having a fluorescent dye to the nucleic acid analysis device; an irradiator for irradiating the nucleic acid analysis device with light; and an emission detector for measuring fluorescence emitted from the fluorescent dye incorporated in a nucleic acid chain due to nucleic acid elongation induced by the coexistence of a nucleotide, a nucleic acid synthetase, and a nucleic acid sample on the nucleic acid analysis device. The nucleic analyzer obtains information on nucleotide sequence of the nucleic acid sample.

In yet another embodiment, the nucleic acid analysis device may further include bonding pads on the support at positions where the microparticles are immobilized, the microparticles are bound to the bonding pads through chemical bonds, the each of the bonding pads have a diameter equal to or less than that of the microparticles, the nucleic acid analysis device further includes a thin-film layer on the support, the thin-film layer including an organic polymer as a material, a part of each bonding pad is exposed from the thin-film layer, and each bonding pad, except for the part, is covered with the thin-film layer.

In an embodiment, a single molecule or two or more molecules of the probe molecule are immobilized on a single microparticle. Two or more probe molecules, when immobilized on a single microparticle, should be of the same type. Probe molecules of different types, if present on a single microparticle, give different signals, and this may impede analysis.

The microparticles may include a material selected from the group consisting of semiconductors, metals, inorganic polymers, and organic polymers. These materials may be spherical or non-spherical.

The bonding pads may include a material selected from the group consisting of gold, titanium, nickel, and aluminum. The smaller thicknesses the bonding pads have, the better. The bonding pads, if having a thickness more than a specific upper limit, could capture two or more microparticles. The bonding pads may have an arbitrary planar shape, such as a circular, square, rectangular, or elliptical shape.

The microparticles for use in the present invention onto which probe molecules are immobilized are often spherical or spheroidal, but are not always spherical and may include amorphous or polygonal particles. The bonding pads to which the microparticles are immobilized need not be spherical. For these reasons, the sizes of the microparticles (spheres) and of the bonding pads (films) are each indicated by an apparent average diameter. Typically, when having a major axis $D_1$ and a minor axis $D_2$, the microparticle has an apparent average diameter D of $(D_1+D_2)/2$. When $D_1$ is equal to $D_2$, D is equal to $D_1$ or $D_2$. Likewise, when having a rectangular, elliptical, or another planar shape and having a long-side length $L_1$ and a short-side length $L_2$, the bonding pad has an apparent average diameter L of $[(L_1^2+L_2^2)]^{1/2}$. When having a square planar shape, the bonding pad has an apparent average diameter L of the square root of $(2L_1)$ or the square root of $(2L_2)$. When having a perfectly circular or a similar planar shape, the bonding pad has an apparent average diameter L of equal to $L_1$ or $L_2$.

The microparticles have sizes (apparent average diameters) of preferably 1 nm to 200 nm, and particularly preferably 5 to 100 nm. The bonding pads have sizes (apparent average diameters) of preferably twice or less, and particularly preferably one time or less the diameters of the microparticles. Though not critical, the bonding pads have thicknesses of preferably 1 nm to 100 nm, and particularly preferably 3 to 50 nm. As used herein the term "diameter(s)" of microparticles and of bonding pads refers to size (s) of the microparticles and of the bonding pads even when the microparticles and the bonding pads include those being not spherical or not having a perfectly circular planar shape, as mentioned above.

The bonding pads have diameters L of preferably twice or less, and more preferably one time or less the diameters of the microparticles. When being non-circular or elliptical, the bonding pads have major axes of preferably twice or less the apparent diameters of the microparticles.

The above and other novel features and advantageous effects of the present invention will be illustrated below with reference to the attached drawings.

The present invention will be illustrated in detail with reference to specific embodiments thereof below, for complete comprehension of the invention. It should be noted, however, that the description below is never construed to limit the scope of the present invention.

First Embodiment

Figure 2:
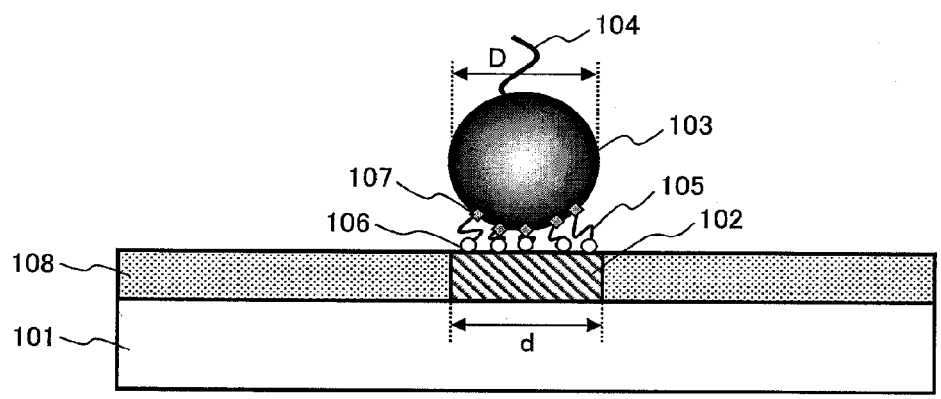
FIG. 2 is a cross-sectional view illustrating a partial configuration as one embodiment of the nucleic acid analysis device illustrated in FIG. 1.

A structure of a device according to the first embodiment will be described with reference to FIGS. 1 and 2. Bonding pads 102 are regularly arranged on a flat (smooth) support 101. The each bonding pads 102 have dimensions of a thickness of 10 nm and a diameter of 40 nm and may be regularly arranged typically in a grid array as illustrated in FIG. 1. This allows the bonding pads to be aligned at uniform intervals. Noise could come into signals if the bonding pads partially excessively approach to each other.

The bonding pads 102 are bound via linear molecules 105 to the microparticles 103 through chemical bonds. A terminal functional group 106 of each linear molecule 105 is preferably bound to a bonding pad 102 through chemical interaction. In this case, the functional group 106 preferably weakly interacts with the flat, smooth support 101 but strongly interacts with the bonding pad 102. From this viewpoint, a quartz glass, sapphire, or silicon support may be used as the flat, smooth support.

The bonding pad 102 may include a material selected from the group consisting of gold, titanium, nickel, and aluminum. The functional group 106 for use herein may be chosen in consideration of the combination of the flat, smooth support 101 and the bonding pad 102 and may be selected typically from sulfhydryl group, amino group, carboxyl group, phosphoric group, and aldehyde group. The linear molecule 105 plays a role of binding the microparticle 103 and the bonding pad 102 to each other, is not significantly limited in length, but is preferably a linear (straight-chain) molecule having about three to about twenty carbon atoms in terms of length.

A terminal functional group 107 of the linear molecule 105 causes adhesion between a microparticle 103 and the linear molecule. A thin film 108 is arranged on the flat, smooth support. The thin film 108 is capable of suppressing non-specific adsorption. The thin film 108 preferably has a thickness equivalent to that of a bonding pad 102 so as to fully cover the lateral side of the bonding pad 102. The thin film 108 preferably includes, as a material, an organic polymer capable of preventing non-specific adsorption of the microparticle 103. Exemplary organic polymers for use herein include polyethylene glycols (PEGs), polyacrylamides, and 3-glycidoxypropylmethoxy silane (GOPS).

Exemplary microparticles 103 for use herein include metal microparticles, semiconductor microparticles, inorganic polymer microparticles, and organic polymer microparticles. Typically, gold microparticles having a diameter of 5 nm to 100 nm are commercially available and are usable herein. Semiconductor microparticles as microparticles of a compound semiconductor, such as CdSe, having diameters of about 10 nm to about 20 nm are commercially available and are usable herein.

Fluorescent emission can be enhanced for observation by using, as the microparticles, microparticles such as gold, silver, platinum, or aluminum microparticles having diameters of about 100 nm or less, because such microparticles can induce localized plasmon excitation at a wavelength within the visible region. For example, fluorescence enhancement by surface plasmon of gold microparticles is reported in Nanotechnology, 2007, vol. 18, pp. 044017-044021 (NPL 4). This enables enhancement of fluorescence from a fluorescent dye bound to a nucleotide for fluorescent detection and increases the signal-to-noise (S/N) level. Particularly when a nucleic acid synthetase is used as the probe molecule 104, a fluorescent dye can be continuously introduced into the electric field enhanced by localized-plasmon, and this advantageously enables stable fluorescence enhancement.

When semiconductor microparticles are used as the microparticles, the observation of fluorescence from the fluorescent dye bound to each nucleotide may be performed by exciting the semiconductor microparticles with light from an external light source and transferring the excitation energy to a fluorescent dye bound to the incorporated nucleotide. In this case, the excitation advantageously requires only a single type of light source, because it is enough for an excitation light source to excite only the semiconductor microparticles. Typically, microparticles having diameters of 15 to 20 nm (product name: "Qdot® streptavidin conjugate" (Invitrogen (Life Technologies Corporation))) may be used.

The inorganic polymer microparticles and organic polymer microparticles are available also as commercial products such as microparticles modified in physical properties such as density, particle size, and electric charge density; microparticles imparted with chemical properties typically by the action of a functional group or spacer; and microparticles labeled typically with a biomolecule such as streptavidin.

Inorganic polymer microparticles, when employed, may be commercially available. Typically, silica microparticles having diameters of 30 to 500 nm are commercially available as inorganic polymer microparticles. They are typified by silica microparticles such as Sicastar®, amino-labeled (micromod Partikeltechnologie GmbH) having diameters of 30 to 500 nm; and Sicastar®, streptavidin-labeled (micromod Partikeltechnologie GmbH) having diameters of 100 to 500 nm.

Organic polymer microparticles may be available as commercial products such as latex microparticles having diameters of 15 to 500 nm, which are typified by Micromer®, amino-labeled (micromod Partikeltechnologie GmbH) having diameters of 15 to 500 nm; and Micromer®, streptavidin-labeled (micromod Partikeltechnologie GmbH) having diameters of 100 to 200 nm, each as latex microparticles. Such amino-labeled microparticles of inorganic polymer or organic polymer may be modified with avidin by reacting microparticles sequentially with biotin-succinimide (NHS-Biotin; Pierce Biotechnology, Inc.) and with streptavidin in this order, as with gold or platinum microparticles. When an oligonucleotide is used as a nucleic-acid-capturing probe 210, the oligonucleotide may be synthesized via terminal modification with biotin. The resulting oligonucleotide can be readily immobilized on a microparticle.

When a nucleic acid synthetase is used as a nucleic-acid-capture probe 104, an expression system may be first established using the RTS AviTag *E. coli* biotinylation kit (Roche Applied Science (Roche Diagnostics Corporation)) to produce a nucleic acid synthetase. The produced nucleic acid synthetase can be readily immobilized on a microparticle. Functional groups usable as the functional group 107 may differ depending on the type of microparticles. For example, when gold microparticles are used, sulfhydryl group or amino group is preferred. When semiconductor microparticles, inorganic polymer microparticles, or organic polymer microparticles are used, commercially available microparticles with surfaces modified with streptavidin may be used. In this case, biotin can be used as the functional group 107.

Figure 3:
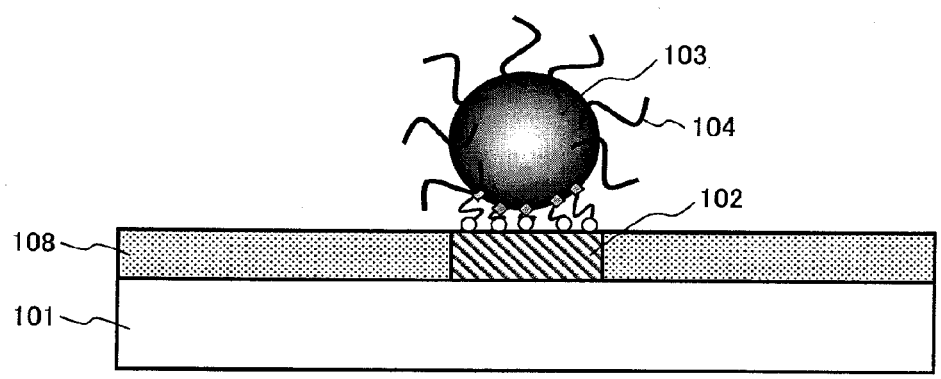
FIG. 3 is a cross-sectional view illustrating a partial configuration as another embodiment of the nucleic acid analysis device illustrated in FIG. 1.

The probe molecule 104 for capturing a nucleic acid may be a single-stranded nucleic acid molecule such as DNA or RNA. One end of the nucleic acid molecule may be previously modified in the above manner as with the functional group 107 to allow the nucleic acid molecule to react with a microparticle 103. A nucleic acid binding protein or nucleic acid synthetase can also be used as the probe molecule 104 for capturing a nucleic acid. A nucleic acid binding protein or nucleic acid synthetase, when synthetically prepared using a specific reagent, can be readily immobilized on the surface of a semiconductor microparticle modified with a commercially available biotin. The specific reagent is a reagent for introducing an avidin tag into an expressed protein and is commercially available. A single-stranded nucleic acid molecule, when used as a probe molecule 104 for capturing a nucleic acid, can capture a sample nucleic acid molecule having a specific complementary sequence. In an embodiment illustrated in FIG. 2, a single probe molecule 104 is immobilized on a single microparticle 103. However, two or more probe molecules may be immobilized on a single microparticle as illustrated in FIG. 3. Even in this case, however, the two or more probe molecules should be of the same type.

Supply of a nucleic acid synthetase or a nucleotide after the capture of the nucleic acid can induce nucleic acid elongation on the support. Likewise, a nucleic acid binding protein, when supplied, can capture a nucleic acid having a specific sequence. A nucleic acid synthetase, when used as the probe molecule 104, could capture a nonspecific sample nucleic acid molecule. Also in this case, supply of nucleotides can induce nucleic acid elongation on the support.

Most preferably, a single probe molecule 104 is immobilized on a single microparticle 103. However, two or more probe molecules may be immobilized on a single microparticle as illustrated in FIG. 3.

When the probe molecule is a short nucleic acid sample fragment, only microparticles each bearing a single probe molecule bound thereto can be selectively obtained after binding the probe molecule to the microparticles. Typically, when microparticles in a number ten times the number of probe molecules were allowed to react with each other, about 90% of microparticles did not capture a probe molecule, but about 9% of microparticles captured each a single probe molecule. This result is in good agreement with a predicted result on the assumption of Poisson distribution. Accordingly, when only microparticles capturing a probe molecule are collected, 90% or more of the collected microparticles are microparticles each capturing only one molecule of probe molecule. The microparticles in this state may be subjected to a process such as separation by molecular weight, collection with magnetic microparticles, or electrophoretic separation using difference in electric charge. This gives microparticles each bearing a single molecule of probe molecule with a higher purity.

Bonding pads 102 may be formed on a flat, smooth support 101 by using a thin film processing which has been practically used in semiconductor technologies. Typically, bonding pads 102 can be prepared by vapor deposition/sputtering through a mask, or by vapor deposition/sputtering to form a thin film and dry or wet etching of the thin film. Regular alignment of bonding pads 102 can be readily achieved using such thin film processing. The distance between pads can be appropriately adjusted. When light detection is performed using a detector, the distance between pads is preferably 500 nm or more in view of the diffraction limit of light detection.

There are various possible ways to detect information related to nucleic acid samples in the nucleic acid analysis device according to the first embodiment. In view of sensitivity and convenience, a method involving fluorescence detection is preferably used. In this case, initially, nucleic acid samples may be supplied to the nucleic acid analysis device so as to allow probe molecules 104 to capture the nucleic acid samples. Next, nucleotides each having a fluorescent dye are supplied thereto. When the probe molecules 104 are DNA probes, a nucleic acid synthetase may be supplied. Nucleic acid elongation may be induced on the device, followed by detection of fluorescence emitted from the fluorescent dye incorporated into nucleic acid chains during the elongation. In this case, a so-called sequential elongation technique can be readily achieved by repeating the steps of supplying one type of nucleotide, washing unreacted nucleotides, observing fluorescent emissions, and supplying another type of nucleotide. After observation of fluorescent emissions, fluorescence from the fluorescent dye may be quenched, or a nucleotide having a fluorescent dye at a phosphate moiety may be used to induce a continuous reaction. Thus, information on the nucleotide sequences of nucleic acid samples can be obtained.

Alternatively, four types of nucleotides having different fluorescent dyes may be supplied and a continuous nucleic acid elongation may be induced without washing, followed by continuous observation of fluorescent emissions. Thus, a so-called real-time reaction process can be realized. In this case, when a nucleotide having a fluorescent dye at a phosphate moiety is used, the phosphate moiety may be cleaved after elongation, and this enables continuous fluorescent detections without quenching, to obtain information on the nucleotide sequences of nucleic acid samples.

Figure 4A:
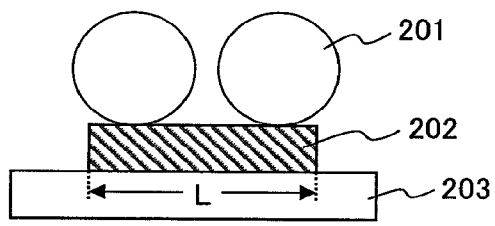
FIG. 4A is a schematic cross-sectional view illustrating an exemplary relationship between the dimensions of a bonding pad formed on a support and the diameters of beads (microparticles) arranged on the bonding pad.
Figure 4B:
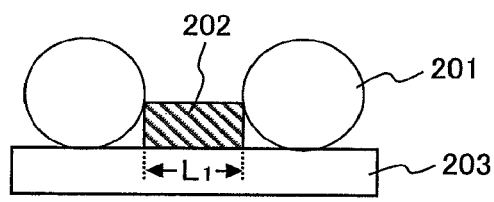
FIG. 4B is a schematic cross-sectional view illustrating another exemplary relationship between the dimensions of a bonding pad formed on a support and the diameters of beads arranged around the bonding pad.

Reasons why a single microparticle 201 is to be immobilized on a bonding pad 202 will be described with reference to FIGS. 4A and 4B. When the microparticles 201 are to be immobilized on bonding pads 202, two or more microparticles 201 could be immobilized on a single bonding pad 202. If two or more microparticles 201 are immobilized thereon, information from different types of nucleic acid fragments are overlapping, and this may impede accurate nucleic acid analysis. Therefore, a single microparticle 201 should be immobilized on a single bonding pad 202. A bonding pad, if having a large diameter L and thereby having a large area as illustrated in FIG. 4A, could capture two microparticles. A bonding pad, if having a large thickness, could adsorb two microparticles and thereby capture two microparticles as illustrated in FIG. 4B, even when the bonding pad has a small diameter L1.

Figure 4C:
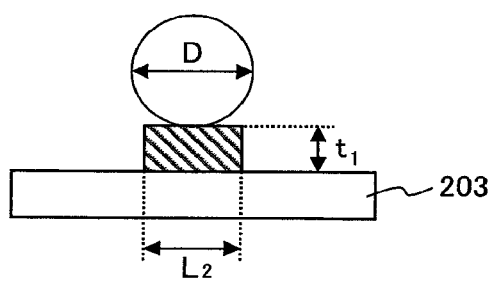
FIG. 4C is a schematic cross-sectional view illustrating still another exemplary relationship between the dimensions of a bonding pad formed on a support and the diameter of a bead arranged on the bonding pad.

To avoid these, the present inventors repeated immobilization experiments under various conditions and made intensive investigations. As a result, they have found that immobilization of a single microparticle 201 to a single bonding pad 202 is achieved when the bonding pad 202 has a diameter L of equal to or less than the diameter D of the microparticle 201, namely, the ratio of the diameter D to the diameter L is equal to or more than 1; and when the surface of the support other than bonding pads is covered with a film for the suppression of non-specific adsorption. Although microparticles repel one another, a single bonding pad, if having an apparent diameter larger than twice that of a microparticle, could capture two or more microparticles even when the film for the suppression of non-specific adsorption is provided in combination. A device illustrated in FIG. 4C includes a bonding pad having an apparent diameter $L_2$ smaller than the apparent diameter D of a microparticle but having a large thickness $t_1$. This device does not employ the film suppressing non-specific adsorption. In this case, the bonding pad could capture microparticles on its lateral side, as illustrated in FIG. 4B.

When a microparticle 201 having a diameter D equal to or more than the diameter L of a bonding pad 202 is immobilized on the bonding pad 202, unreacted linear molecules may be covered with the immobilized microparticle 201 and prevented from reacting with another microparticle 201.

In consideration of this, a bonding pad preferably has a thickness ($t_2$) as small as possible. This is because, if a bonding pad 202 has a large thickness and thereby has a large lateral-side area, two or more microparticles 201 could be immobilized on a single bonding pad 202 even when the bonding pad 202 has a diameter equal to or less than the diameter of the microparticles 201.

Figure 5:
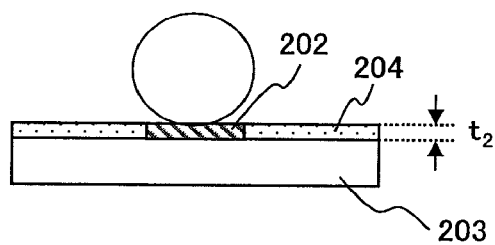
FIG. 5 is a schematic cross-sectional view illustrating an exemplary relationship between the dimensions of a bonding pad formed on a support and the diameter of a bead arranged on the bonding pad, according to an embodiment of the present invention.
Figure 6:
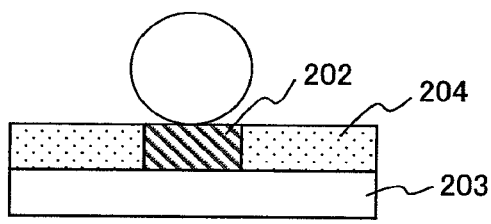
FIG. 6 is a schematic cross-sectional view illustrating an exemplary relationship between the dimensions of a bonding pad formed on a support and the diameter of a bead arranged on the bonding pad, according to another embodiment of the present invention.

However, according to an embodiment of the present invention, immobilization of two or more microparticles 201 to a single bonding pad 202 can be prevented even when the bonding pad 202 has a relatively large thickness. This is achieved by covering the lateral side of the bonding pad 202 with an organic polymer 204, such as a PEG (polyethylene glycol), which suppresses adsorption of a biomolecule, as illustrated in FIGS. 5 and 6. This eliminates the influence of the thickness of bonding pad on the number of microparticles to be immobilized. The present invention therefore enables easy control of the thicknesses of bonding pads upon formation and provides a higher production yield.

A process of covering the lateral side of a bonding pad 202 with a PEG using a silane coupling agent in a nucleic acid analysis device will be described. This process employs a PEG-silane agent prepared by polymerization of a PEG with a silane coupling agent. The PEG-silane agent for use herein is typified by 2-[methoxy(polyethylene-oxy)propyl]-trimethoxysilane (Gelest, Inc.). A PEG-silane film having a thickness equivalent to the thickness of a bonding pad 202 is formed in the nucleic acid analysis device. A single-layer PEG-silane film has a thickness of about 1 nm. When this thickness is less than the thickness of the bonding pad 202, a multilayered PEG-silane film may be prepared so as to have a thickness equivalent to the thickness of the bonding pad 202. The film was prepared in the following manner. The PEG-silane agent was dissolved in a solvent to give a solution, a catalyst such as triethylamine was added to the solution to give a mixture, and the nucleic acid analysis device was immersed in the mixture at 60° C. for one hour.

The nucleic acid analysis device was retrieved from the mixture and baked in an electric furnace at 130° C. for one hour. A thickness of a silane film on the support was measured with a spectroscopic ellipsometer. The measurement demonstrated the presence of a silane film having a thickness of 14 nm. It was also demonstrated that the thickness of film can be controlled in the range of 1 to 14 nm by modifying reaction conditions such as the concentration of the PEG-silane agent, baking temperature, and baking time. A PEG-silane film having a thickness of 10 nm was actually formed on a nucleic acid analysis device having a bonding pad 202 with a thickness of 10 nm. As a result, the lateral side of the bonding pad 202 could be covered with the PEG-silane film. This was verified by observation of the cross section of the nucleic acid analysis device under a scanning electron microscope (SEM).

Bonding pads of some materials may be covered with the PEG-silane film also on the top side. In this case, the binding of the PEG-silane agent to the top side of a bonding pad can be prevented by covering the bonding pad 202 typically with a molecule capable of inhibiting silanol adsorption, prior to the treatment to form a PEG-silane film. For example, when the flat, smooth support 203 is made of a quartz glass and the bonding pad 202 is made of titanium oxide, a poly(vinylphosphoric acid) (PVPA) can be used as the molecule capable of inhibiting silanol adsorption, to cover titanium oxide alone. Such poly(vinylphosphoric acid) (PVPA) is adsorbed on titanium oxide but is not adsorbed on quartz glass.

Only a PEG-silane film present on the top side of a bonding pad can be removed according to the difference in adsorption power of the PEG-silane film, even when the molecule capable of inhibiting silanol adsorption is not used. Specifically, a PEG-silane film is more weakly adsorbed on a metal or metal oxide constituting a bonding pad than on a quartz glass or sapphire constituting a flat, smooth support 301, and only a PEG-silane film present on the bonding pad can be removed by a cleaning step using ultrasound or a surfactant. The present inventors actually verified that, when a PEG-silane film was prepared so as to have a thickness equivalent to that of a bonding pad 202, only the lateral side of the bonding pad 202 could be fully covered with the PEG-silane film by covering the prepared bonding pad 202 with a molecule capable of inhibiting silanol adsorption before the formation of the PEG-silane film, or by removing the formed PEG-silane film through cleaning. The resulting nucleic acid analysis device including the PEG-silane film fully covering only the lateral side of the bonding pad 202 was allowed to react with a microparticle 201 whose surface had been modified with avidin. As a result, the microparticle 201 was immobilized onto the top side of the bonding pad 202 but was not immobilized to the lateral side thereof. This was verified through observation under a scanning electron microscope (SEM).

As is described above, the organic polymer (film) 204 for preventing non-specific adsorption could be easily prepared on a nucleic acid analysis device. This enabled highly effective prevention of non-specific adsorption and indicated significant noise reduction. This also remarkably improved the percentage of immobilization of microparticles 201 to bonding pads 202 on a one-to-one basis. These improvements help the nucleic acid analysis device to have a remarkably higher throughput.

Second Embodiment

Embodiments relating to a method for producing a nucleic acid analysis device will be illustrated with reference to FIGS. 7 and 8.

Figure 7:
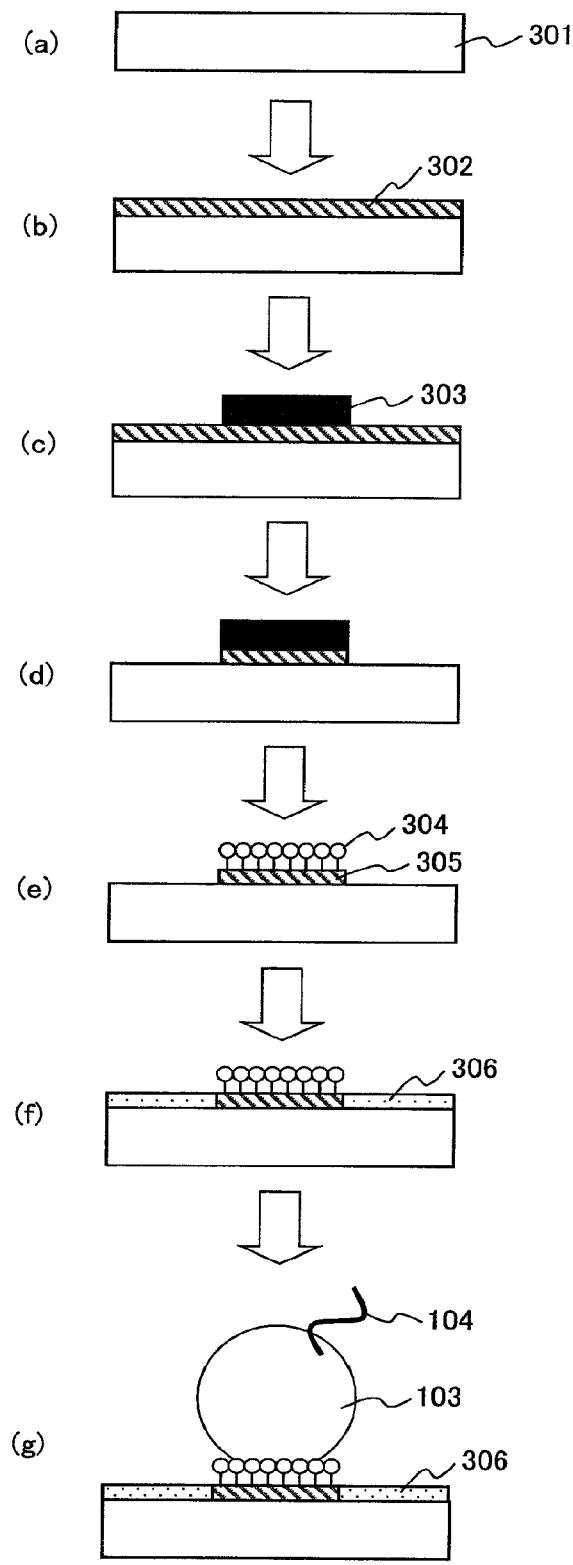
FIG. 7 is a flowchart illustrating a method for producing a nucleic acid analysis device according to an embodiment of the present invention.
Figure 8:
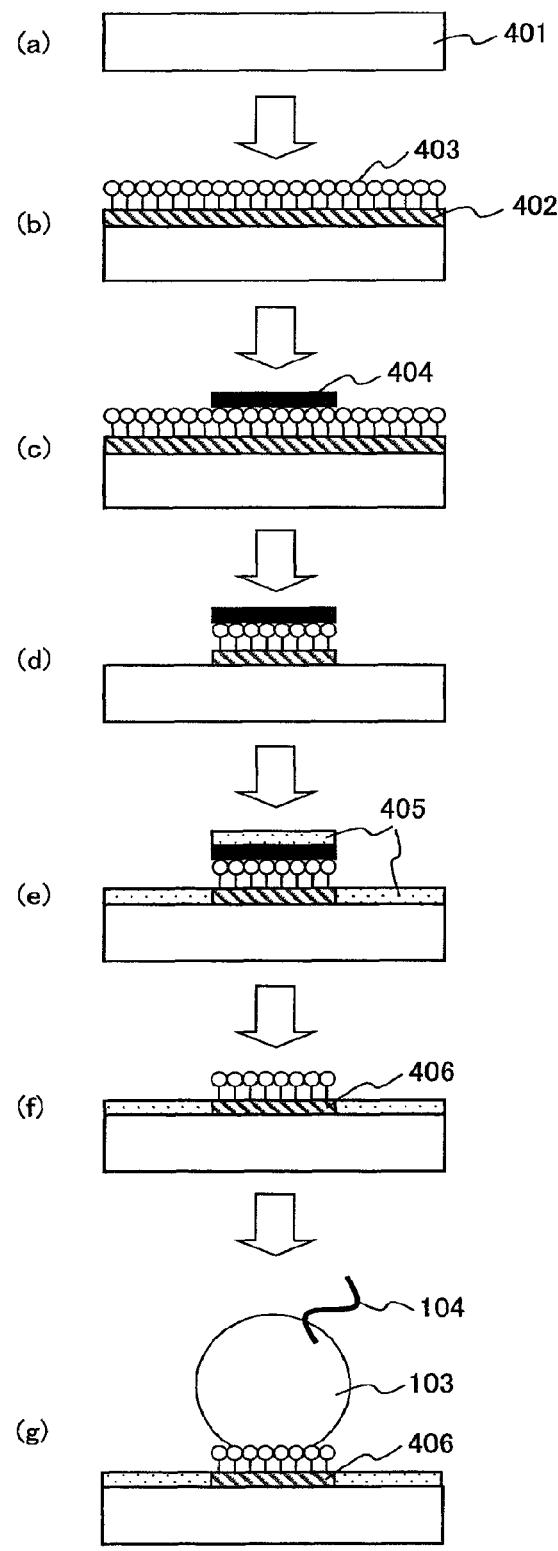
FIG. 8 is a flowchart illustrating a method for producing a nucleic acid analysis device according to another embodiment of the present invention.

In an embodiment illustrated in FIG. 7, a film of a material for constituting a bonding pad 305 is deposited on a flat, smooth support 301 by sputtering (FIG. 7 (b)) to form a thin metal film 302. The material is typified by gold, titanium, nickel, or aluminum. When the flat, smooth support 301 is a glass support or sapphire support, and when the bonding pad 305 is to be formed from gold, aluminum, or nickel, a thin film of titanium or chromium is preferably deposited between the support and the bonding pad 305 so as to enhance adhesion between the material constituting the support and the material constituting the bonding pad 305.

A resist pattern 303 is formed on the thin metal film 302 (FIG. 7 (c)). Next, the thin metal film 302 in a region other than the resist pattern is removed by etching (FIG. 7 (d)). The resist 303 is then removed to complete a bonding pad 305. Next, linear molecules 304 are allowed to react with the flat, smooth support 301 (FIG. 7 (e)). The linear molecules 304 are not adsorbed on the flat, smooth support 301 but adsorbed on the bonding pad 305. When the bonding pad 305 is made from gold, titanium, aluminum, or nickel, the linear molecules 304 each preferably have a sulfhydryl group, phosphoric group, or thiazole group as a terminal functional group. The linear molecules may have biotin as a functional group. After the reaction of the linear molecules with the flat, smooth support 301, a thin film 306 is prepared on the surface of the flat, smooth support 301 except for a region where the bonding pad 305 has been formed (FIG. 7(f)).

Next, a microparticle 103 is bound to the linear molecules 304 through chemical bonds, and one or plural probe molecules are immobilized on the surface of the microparticle (FIG. 7 (g)).

The thin film 306 includes a material organic polymer for preventing non-specific adsorption of the microparticle 103. The type of the organic polymer for preventing non-specific adsorption is suitably selected depending on the surface condition of the microparticle 103. A negatively-charged organic polymer is selected when the microparticle 103 has a negatively charged surface, so as to repel each other. A hydrophobic organic polymer is selected when the microparticle 103 has a hydrophilic surface; whereas a hydrophilic polymer is selected when the microparticle 103 has a hydrophobic surface. Typically, a polyethylene glycol (PEG), a polyacrylamide, or 3-glycidoxypropylmethoxysilane (GOPS) may be used as the organic polymer 306 for preventing non-specific adsorption when the microparticle 103 is one modified with hydrophilic avidin.

Another embodiment of a method for producing a nucleic acid analysis device will be illustrated with reference to FIG. 8. This method allows linear molecules 403 to remain only on the top side of a bonding pad 406 even when the linear molecule does not have selectivity between the bonding pad 406 and a flat, smooth support 401.

With reference to FIG. 8(b), the linear molecules 403 is allowed to react before etching of a deposited thin metal film 402. In this case, a pattern is formed with a resist 404 after the reaction of the linear molecules 403 (FIG. 8(c)). The thin metal film 402, other than the region protected by the resist 404, is removed together with the linear molecules 403 by etching (FIG. 8(d)). Next, a thin film of an organic polymer 405 for preventing non-specific adsorption is formed on the resist 404 and the flat, smooth support 401 (FIG. 8(e)).

The resist 404 is then stripped to thereby remove the resist 404 together with the organic polymer 405 for preventing non-specific adsorption formed on the resist 404. Thus, a bonding pad bound to a patterned linear molecule 403 is formed (FIG. 8(f)). A microparticle 103 is then bound to the linear molecules 403 through chemical bonds, and one or plural probe molecules are immobilized on the surface of the microparticle (FIG. 8(g)).

The microparticles have preferably been modified with avidin on surface. When gold or platinum microparticles are used, modification with avidin can be easily performed by allowing the microparticles to react sequentially with aminothiol, biotin-succinimide (NHS-Biotin; Pierce Biotechnology, Inc.), and streptavidin in this order. When microparticles of another metal than gold and platinum are used, surface modification of the metal microparticles with avidin can be easily performed by subjecting the microparticles to heating in an oxygen atmosphere to oxidize the surface, and allowing the surface-oxidized microparticles to react sequentially with aminosilane, biotin-succinimide (NHS-Biotin; Pierce Biotechnology, Inc.), and streptavidin in this order.

The each of the microparticles bearing a nucleic-acid-capturing probe immobilized thereon are then allowed to react with the flat, smooth support 401 and thereby yields a nucleic acid analysis device according to the second embodiment.

Third Embodiment

Figure 9:
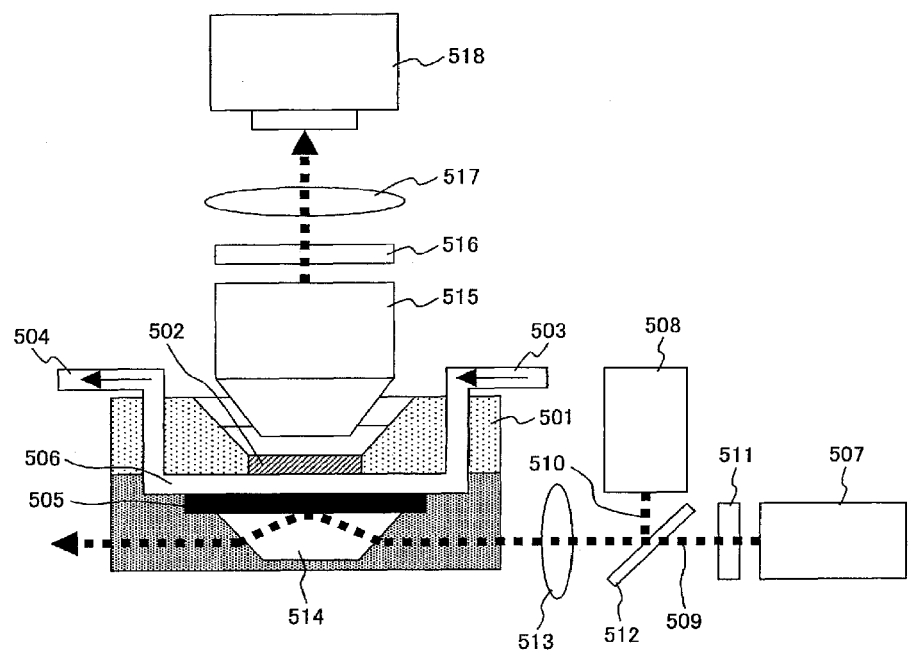
FIG. 9 is a diagram illustrating an exemplary configuration of a nucleic acid analyzer including a nucleic acid analysis device according to the present invention.

In the third embodiment, an exemplary preferred configuration of a nucleic acid analyzer using a nucleic acid analysis device will be illustrated with reference to FIG. 9. The nucleic acid analyzer according to the third embodiment includes a nucleic acid analysis device; a supplier for supplying a nucleic acid synthetase, a nucleic acid sample, and a nucleotide having a fluorescent dye to the nucleic acid analysis device; an irradiator for irradiating the nucleic acid analysis device with light; and an emission detector for detecting fluorescence emitted from the fluorescent dye incorporated into a nucleic acid chain through nucleic acid elongation that is induced by the coexistence of a nucleotide, a nucleic acid synthetase, and a nucleic acid sample on the nucleic acid analysis device. More specifically, the device 505 is placed in a reaction chamber which includes a cover plate 501, a detection window 502, an inlet 503, and an outlet 504, which inlet and outlet serve as solution exchange ports. A polydimethylsiloxane (PDMS) may be used as a material for the cover plate 501 and the detection window 502.

The detection window 502 may have a thickness of 0.17 mm. A yttrium-aluminum-garnet (YAG) laser source (wavelength: 532 nm; output 20 mW) 507 and a YAG laser source (wavelength: 355 nm; output: 20 mW) 508 emit laser beams 509 and 510, respectively. The laser beam 509 alone is circularly polarized using a quarter-wave plate (λ/4 plate) 511 so as to adjust the two laser beams concentrically with a dichroic mirror 512 (for reflecting light with a wavelength of 410 nm or less), followed by light condensing using a lens 513. Then, the device 505 is irradiated with the light (laser beam) via a prism 514 at an angle equal to or larger than the relevant critical angle.

An example in which gold microparticles each having a diameter of approximately 50 nm are used as microparticles is described below.

In this case, localized surface plasmon is generated on gold microparticles present on the surface of a device 505 via laser irradiation. Accordingly, a fluorophore of a target substance captured by a DNA probe bound to a gold microparticle is present in the enhanced electric field. A fluorophore is excited with laser light, and the enhanced fluorescent emission is partially output through the detection window 502. A parallel light beam is formed with fluorescence passed through the detection window 502 using an objective lens 515 (x60; NA=1.35; operating distance: 0.15 mm). Background light and excitation light are then intercepted by an optical filter 516, resulting in imaging with a two-dimensional CCD camera 518 via an imaging lens 517.

When a sequential reaction system is employed, an exemplary nucleotide having a fluorescent dye usable herein is a nucleotide including a 3'-O-allyl group is added as a protective group at the 3' OH position of ribose moiety; and a fluorescent dye bound via an allyl group at the 5-position of pyrimidine or the 7-position of purine, as disclosed in NPL 5. The allyl group may be cleaved by light irradiation (at a wavelength typically of 355 nm) or by contact with palladium. This enables both quenching of light emitted from a dye and control of elongation. Even in the case of a sequential reaction, there is no need to remove unreacted nucleotides by cleaning. Additionally, real-time measurement during elongation is also possible, because a cleaning step is not necessary. In this case, there is no need to add a 3'-O-allyl group as a protective group at the 3' OH position of ribose moiety in the nucleotide. A nucleotide bound to a dye via a functional group capable of being cleaved by light irradiation (at a wavelength typically of 355 nm) may be used.

When semiconductor microparticles are used as the microparticles, the above example of a nucleic acid analyzer can also be applied. For example, when a Qdot® 565 (Invitrogen (Life Technologies Corporation)) is used as a semiconductor microparticle, sufficient excitation can be induced using a YAG laser source 507 (wavelength: 532 nm; output: 20 mW). When the excitation energy is transferred to Alexa Fluor® 633 (Invitrogen (Life Technologies Corporation)) that is not excited with light at a wavelength of 532 nm, fluorescence emission occurs. Specifically, a dye bound to an unreacted nucleotide is not excited. Only after a nucleotide bound to a dye is captured by a DNA probe and thus becomes in proximity to a semiconductor microparticle, which results in energy transfer, light is emitted from the dye. Captured nucleotides can therefore be identified by fluorometry.

Microparticles made from an inorganic polymer or organic polymer are not excited even upon irradiation with light from an external light source. For this reason, light emission from a fluorescent dye due to transfer of excitation energy does not occur, whereas unreacted nucleotides also emit light, and this may cause noise. However, incorporated nucleotides alone can be allowed to emit light by binding a nucleic acid synthetase to a microparticle capable of inducing energy transfer, such as a semiconductor microparticle. Alternatively, fluorescence from such incorporated nucleotides can be enhanced by binding gold, silver, platinum, or aluminum to a nucleic acid synthetase. Fluorescence around a metal pad for immobilizing a microparticle can be enhanced, and thereby the signal-to-noise ratio can be increased by using gold, silver, platinum, or aluminum as a material for constituting the metal pad.

As is described above, when a nucleic acid analyzer is assembled using the nucleic acid analysis device according to the third embodiment, analysis time can be shortened without introducing a cleaning step into the analysis process, and the device and the analyzer can be simplified. Accordingly, not only measurement based on a sequential reaction system but also real-time measurement can be achieved during nucleotide elongation. This provides significant throughput improvement over customary techniques.

According to the present invention, many types of nucleic acid fragments can be regularly aligned at a high density and immobilized on a support by the medium of microparticles. This allows immobilization of a single molecule of nucleic acid sample fragment at a high percentage merely by a simple treatment of the support without increasing the number of steps in production process of a nucleic acid analysis device; and also enables noise reduction by suppression of non-specific adsorption of microparticles. This in turn enables low-cost and high-throughput analysis of nucleic acid samples.

REFERENCE SIGNS LIST

101, 203, 301, 401 flat, smooth support
102, 202, 305 bonding pad
103, 201 microparticle
104 probe molecule
105 linear molecule
106, 107, 205, 206, 304, 403 terminal functional group of linear molecule
108, 204, 306, 405 organic polymer for preventing non-specific adsorption
302, 402 thin metal film
303, 404 resist
501 cover plate
502 detection window
503 inlet
504 outlet
505 nucleic acid analysis device
506 flow channel
507, 508 YAG laser source
509, 510 laser beam
511 quarter-wave plate
512 dichroic mirror
513 lens
514 prism
515 objective lens
516 optical filter
517 imaging lens
518 two-dimensional CCD camera

The invention claimed is:
1. A method for producing a nucleic acid analysis device which comprises the steps of:
   forming a metal film on a surface of a support;
   selectively etching the metal film to form a plurality of bonding pads;
   introducing a linear molecule into each of the bonding pads, the linear molecule capable of being adsorbed on the bonding pad;
   forming a second film for preventing adsorption of microparticles on the surface of the support and the side of the bonding pad excluding the surface of the bonding pad;
   selectively binding each of the microparticles to the linear molecule being on the bonding pad through a chemical bond; and
   immobilizing a probe molecule or molecules to each of the microparticles through a chemical bond,
   wherein the second film has a thickness equivalent to that of each of the bonding pads, and
   wherein the bonding pads have diameters each being twice or less than the diameters of the microparticles.
2. The method for producing a nucleic acid analysis device of claim 1, wherein the second film is a PEG-silane film being formed on the surface of the support excluding the bonding pad by coating an adsorption inhibitor for inhibiting adsorption with PEG-silane film so as to cover the surface of the support including the bonding pad and by selectively forming the adsorption inhibitor on the bonding pad.

3. The method for producing a nucleic acid analysis device of claim 1, wherein the bonding pads are regularly arranged on the support.

4. The method for producing a nucleic acid analysis device of claim 1, wherein two or more probe molecules are immobilized on a single microparticle.

5. A method for producing a nucleic acid analysis device which comprises the steps of:
 forming a metal film on a surface of a support;
 selectively etching the metal film to form a plurality of bonding pads;
 introducing a linear molecule into each of the bonding pad, the linear molecule capable of being adsorbed on the bonding pad;
 forming a second film having more weak adsorption power on the bonding pad rather than on the surface of the support and preventing adsorption of microparticles so as to cover the surface of the support including the bonding pad;
 selectively removing the second film on the bonding pad using the difference in the adsorption power between the surface of the support and the bonding pad;
 selectively binding each of the microparticles to the linear molecule being on the bonding pad through a chemical bond; and
 immobilizing a probe molecule or molecules to each of the microparticle through a chemical bond,
 wherein the second film has a thickness equivalent to that of each of the bonding pads, and
 wherein the bonding pads have diameters each twice or less the diameters of the microparticles.

6. The method for producing a nucleic acid analysis device of claim 5, wherein the second film is a PEG-silane film and the removing step is performed in a cleaning step using ultrasound or a surfactant.

7. The method for producing a nucleic acid analysis device of claim 5, wherein the bonding pads are regularly arranged on the support.

8. The method for producing a nucleic acid analysis device of claim 5, wherein two or more probe molecules are immobilized on a single microparticle.

* * * * *